United States Patent [19]

Smernoff

[11] Patent Number: 4,604,263
[45] Date of Patent: Aug. 5, 1986

[54] CELL FOR GAS SAMPLE EQUILIBRATOR

[75] Inventor: Ronald B. Smernoff, Belmont, Calif.

[73] Assignee: Analytical Products, Inc., Belmont, Calif.

[21] Appl. No.: 697,268

[22] Filed: Jun. 17, 1976

[51] Int. Cl.[4] .................. G01N 33/50; G01N 1/00; B01L 11/00
[52] U.S. Cl. .................................. 422/50; 55/68; 422/68; 422/81; 422/99; 422/101; 436/68; 436/11; 436/174; 436/178; 261/82
[58] Field of Search ............ 23/232 R, 230 B, 253 R, 23/254 R, 258.5; 55/68; 422/68, 81, 50, 89, 101; 436/68, 11, 174, 178; 261/82

[56] References Cited

U.S. PATENT DOCUMENTS 3,127,254  3/1964  Astrup et al. ................. 55/68
3,973,915  8/1976  Raffaele et al. ............... 23/259

OTHER PUBLICATIONS

Noonan et al, Clinical Chem., vol. 20, No. 6, 1974 pp. 660-665.

Primary Examiner—Michael S. Marcus
Attorney, Agent, or Firm—Fliesler, Dubb, Meyer & Lovejoy

[57] ABSTRACT

Cell useful for equilibrating a hydrophilic liquid such as an aqueous solution held therewithin with a gas composition. The cell comprises a tube having an open end and a closed end, the closed end comprising a porous member having a hydrophobic surface, the member being impervious to flow of a hydrophilic liquid therethrough when the tube is filled therewith and positioned vertically with a closed end thereof downwardly and being permeable to pressurized flow of the gas composition upwardly therethrough. The invention is also concerned with such a cell in an apparatus for equilibrating a hydrophilic liquid such as an aqueous solution with a gas composition, which apparatus comprises a gas vessel having therewithin a gas of a selectable composition at a pressure above ambient atmospheric pressure, flow control means for receiving flow from said vessel and controlling a flow rate therefrom and conduit means leading from the flow control means to a solution cell having therewithin a hydrophilic liquid.

16 Claims, 15 Drawing Figures

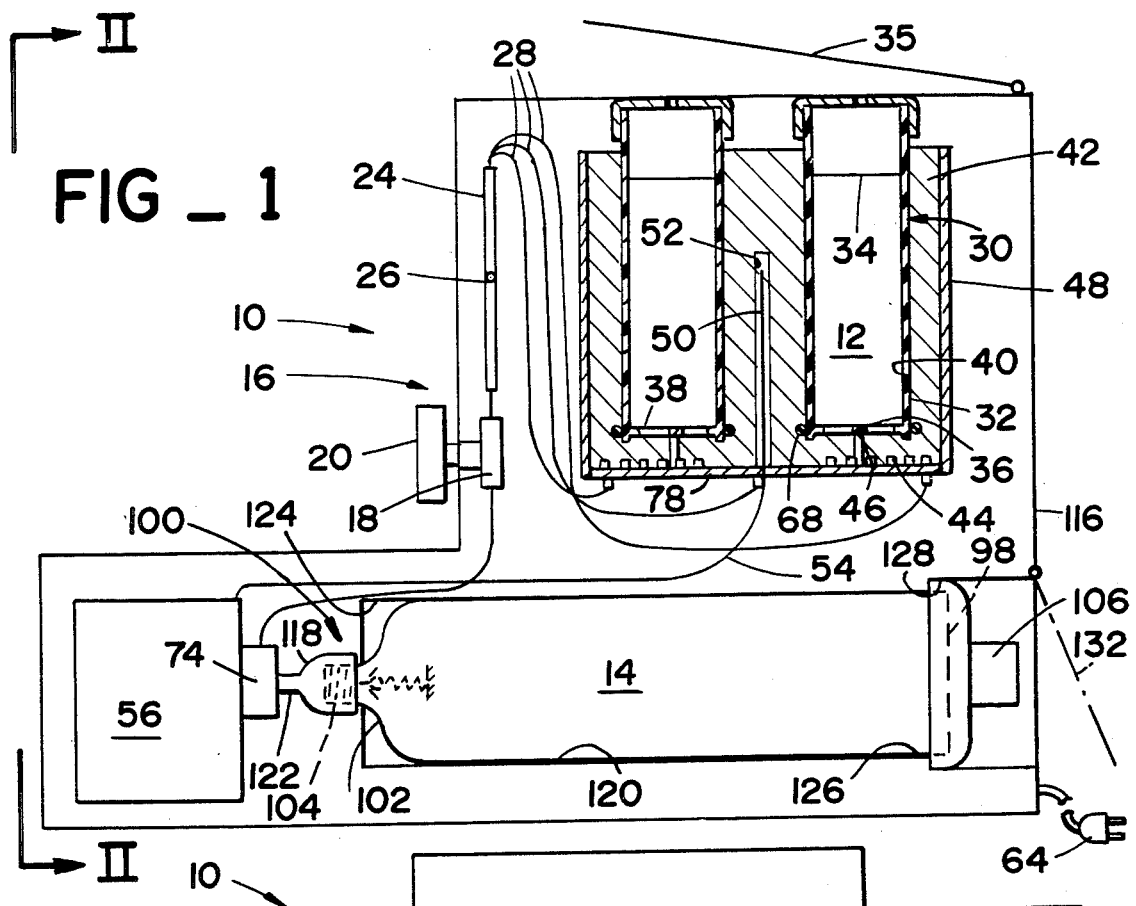
FIG_1
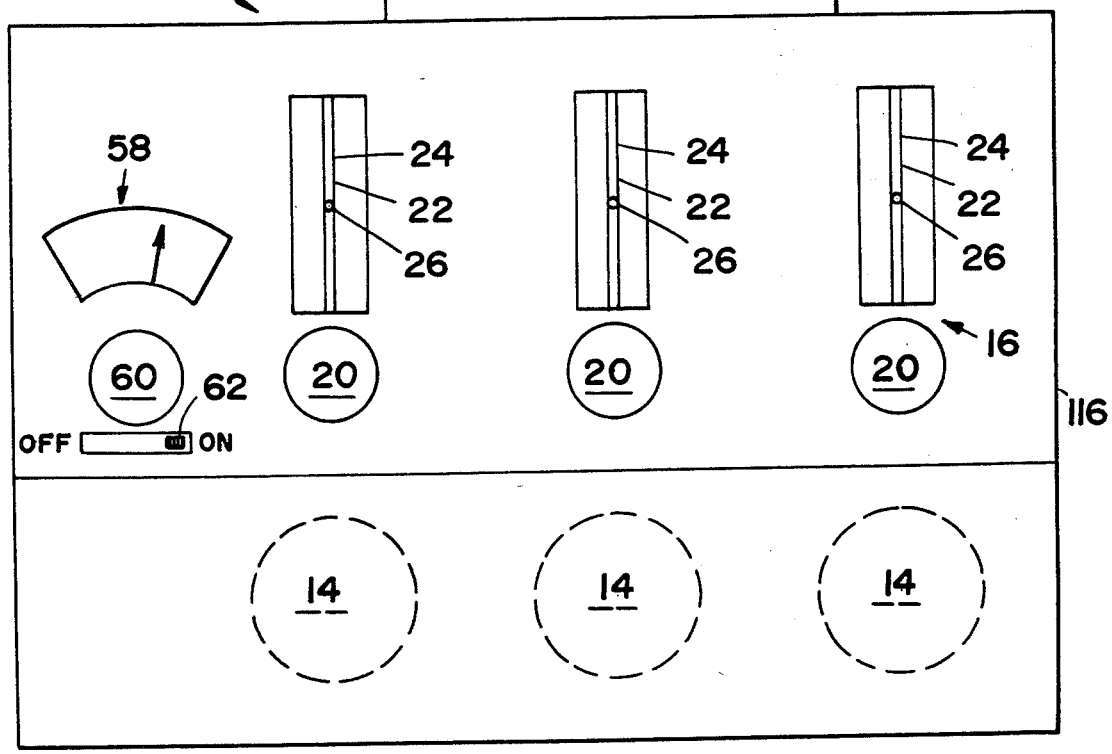
FIG_2

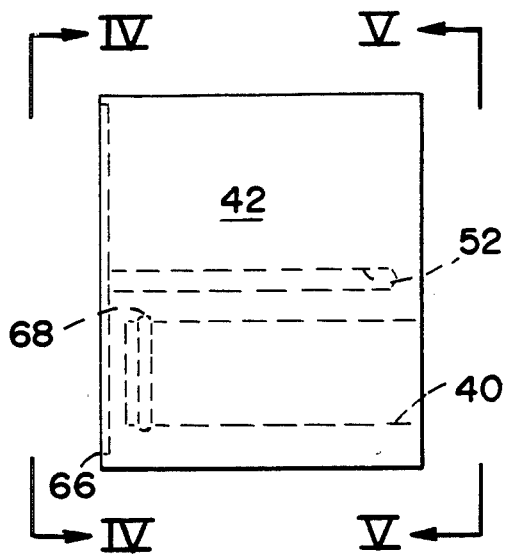
FIG_3
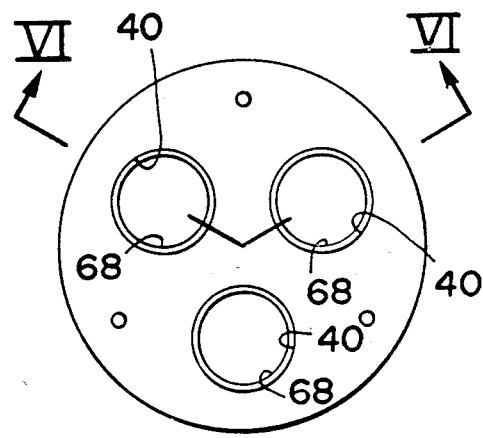
FIG_5
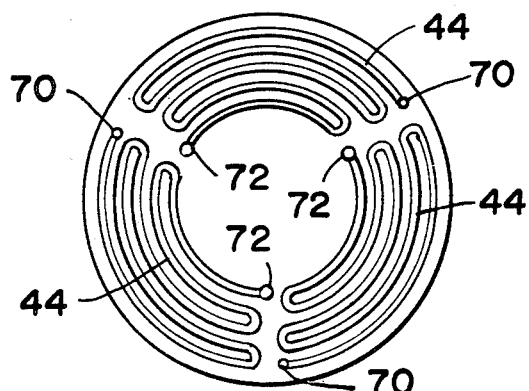
FIG_4
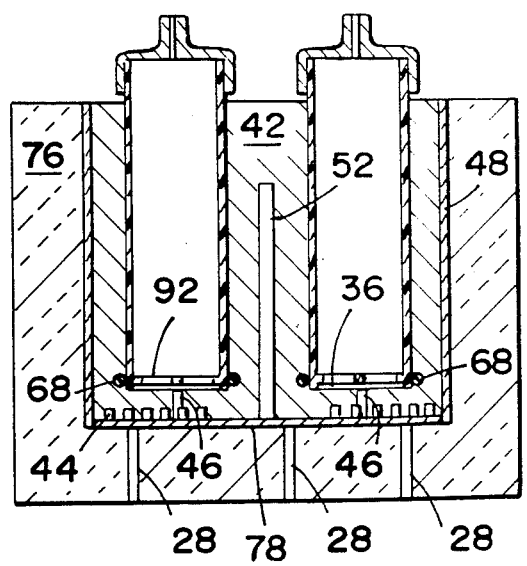
FIG_6
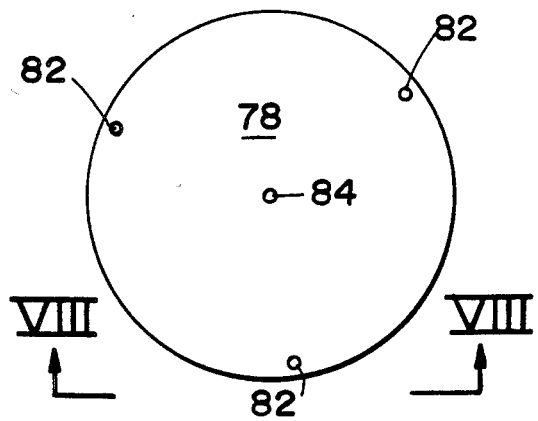
FIG_7
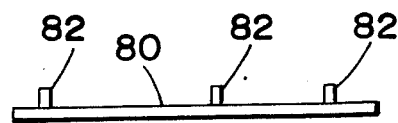
FIG_8

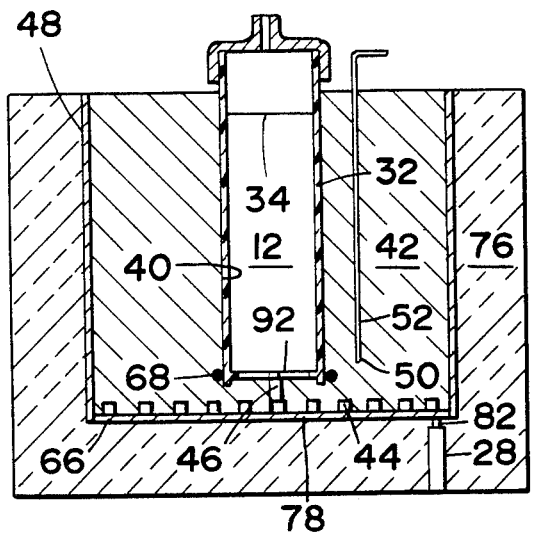
FIG_9
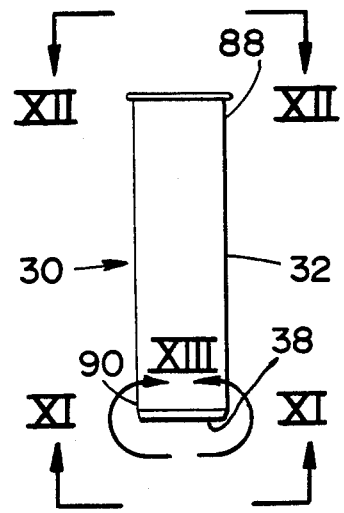
FIG_10
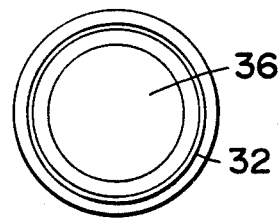
FIG_11
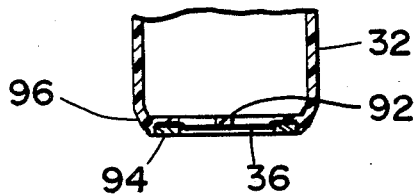
FIG_13
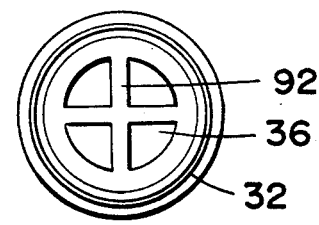
FIG_12
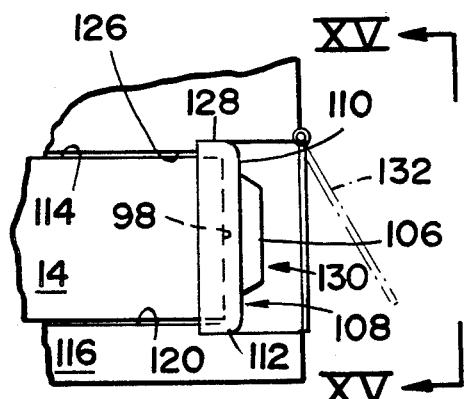
FIG_14
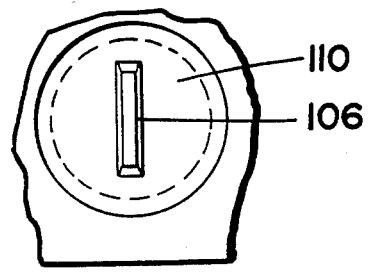
FIG_15

1

CELL FOR GAS SAMPLE EQUILIBRATOR

BACKGROUND OF THE INVENTION

1. Field of the Invention

The invention is concerned with cells which are useful for equilibrating a hydrophilic liquid such as an aqueous solution held therewithin with a gas composition. More particularly the invention is concerned with such cells as are particularly useful for equilibrating standard and tests solutions for calibrating blood-gas analysis instruments.

PRIOR ART

The prior art teaches equilibrating gas compositions with liquids which are to be used as standards and/or test samples for blood-gas analyzers. Particularly, the prior art teaches blowing the gas which is to be equilibrated with an aqueous solution on to the surface thereof either with oscillation of the solution to aid in mixing or with centrifuging of the solution to be equilibrated to increase its surface area. The cells used to accomplish such equilibrating do not provide for introducing the gas to be equilibrated with a particular solution below the surface thereof in the form of bubbles. As a result, equilibration takes a good deal of time, generally twenty to thirty minutes per sample. Also, the prior art apparatus which utilizes such cells generally only handle one cell at a time whereby it is necessary to use one to one and one-half hours to produce a standardization sample for calibrating a blood-gas analyzer and two samples for testing the accuracy of such a calibration. Most medical laboratories operate three shifts on a twenty-four hour day. It is common practice to recalibrate blood-gas analyzers at the start of each shift partially because of the change in personnel. Thus, from about one to about one and one-half hours is generally consumed in simply preparing a standard and a pair of test samples for calibrating and testing the accuracy of calibration of each blood-gas analyzer in the laboratory at the start of each shift. It is clear that this results in considerable downtime thus increasing the costs and time involved in obtaining accurate blood-gas analysis results.

It would be very advantageous to provide a cell which would be useful for equilibrating an aqueous solution held therewithin with a gas composition in a short period of time whereby operation of standard and test samples for blood-gas analyzers and other similar instrumentation could be very significantly reduced, perhaps down to as little as three to four minutes per eight hour shift. The present invention is concerned with just such an improved cell.

SUMMARY OF THE INVENTION

In one sense the invention comprises a cell useful for equilibrating a hydrophilic liquid such as an aqueous solution held therewithin with a gas composition. The cell comprises a tube having an open end and a closed end, said closed end comprising a porous member having a hydrophobic surface, said member being impervious to flow of a hydrophilic liquid such as an aqueous solution therethrough when said tube is filled therewith and positioned vertically with the closed end thereof downwardly and being permeable to pressurized flow of said gas composition upwardly therethrough.

In another sense the invention is concerned with an improved cell as set out above as used in an apparatus for equilibrating a hydrophilic liquid such as an aqueous solution with a gas composition which comprises a gas vessel having therewithin a gas of a selectable composition at a pressure above ambient atmospheric pressure, flow control means for receiving flow from said vessel and controlling a flow rate therefrom and conduit means leading from said flow control means to a solution cell having therewithin a hydrophilic liquid such as an aqueous solution. The cell as improved above provides extremely fast attainment of gas-solution equilibrium.

It is an object of the present invention to provide an improved cell useful for attaining fast gas-solution equilibrium.

It is a further object of the present invention to provide such a cell for us in an apparatus for preparing samples and standards for blood-gas analyzer calibration and testing.

It is a still further object of the present invention to greatly reduce the time needed to prepare standard and test solutions for calibration and testing of blood-gas analyzers.

These and other objects of the invention as will become apparent from reading the description that follows are accomplished through use of a cell as claimed herein.

BRIEF DESCRIPTION OF THE DRAWINGS

The invention will be better understood by reference to the figures of the drawings wherein like numbers denote like parts throughout and wherein:

FIG. 1 illustrates in side section an apparatus in accordance with the present invention;

FIG. 2 illustrates a view taken along the line II—II of FIG. 1;

FIG. 3 illustrates in side elevation a heating block useful in the apparatus of the present invention;

FIG. 4 illustates a view taken along the line IV—IV of FIG. 3;

FIG. 5 illustrates a view taken along the line V—V of FIG. 3;

FIG. 6 illustrates a view taken along the line VI—VI of FIG. 5;

FIG. 7 illustrates a detail in a construction of apparatus useful in the practice of the present invention;

FIG. 8 illustrates a view taken along the line VIII—VIII of FIG. 7;

FIG. 9 illustrates an alternate embodiment of the view shown in FIG. 6 wherein the block includes a single cavity and a single cell;

FIG. 10 illustrates an improved cell in accordance with the present invention;

FIG. 11 illustrates a view taken along the line XI—XI of FIG. 10;

FIG. 12 illustrates a view taken along the line XII—XII of FIG. 10;

FIG. 13 illustrates a blown-up view of the area XIII—XIII of FIG. 10, in section;

FIG. 14 illustrates a blown-up view of a cylinder end with a handle extending therefrom useful in the practice of the present invention; and FIG. 15 illustrates a view taken along the line XV—XV of FIG. 14.

DETAILED DESCRIPTION OF THE PREFERRED EMBODIMENTS

The present invention is particularly concerned with an apparatus 10 shown in its entirety in FIGS. 1 and 2 for equilibrating a hydrophilic liquid which will not wet a hydropholic surface (will not have a 90° contact angle therewith, as discussed, e.g., in Modern Colloids by Robert B. Dean, D. Van Nostrand Company, Inc. New York, 1948 at pages 62–66.) such as an aqueous solution, more generally a plurality of aqueous solutions 12, with a gas contained within one of a plurality of gas vessels 14. Each of the gas vessels 14 has therewithin a gas of a selectable composition at a pressure above ambient atmospheric pressure. Flow control means 16, in the embodiment illustrated in FIGS. 1 and 2 a plurality of flow control means 16 comprising a plurality of needle valves 18 each having knobs 20 and each leading to flow meters 22, which flow meters 22 generally comprise a tube 24 having a ball 26 suspended therein by the air flowing through the valve 18 each conduct gas via a plurality of lines 28, one to each of a plurality of cells 30, each of which in the embodiment illustrated comprises a sample tube 32. As will be noted, each of the plurality of lines 28 leads from the respective flow meter 22 to the tube 32 below a liquid level 34 of the aqueous solution 12. A hinged cover 35 is generally provided to assure non-contamination of the solution 12.

Means are also provided for causing the gas to be delivered within the aqueous solution while below the liquid level 34 as a plurality of fine bubbles. In the particular embodiment illustrated in FIG. 1 for example, the bubble delivering means comprises a plurality of membranes 36 each of which fits across a closed end 38 of a respective solution tube 32.

The solution tubes 32 fit within one of a plurality of cavities 40 formed within a heat conductive block 42. Thus, through adjustment of the temperature of the block 42 the temperature of each of the solutions 12 can be controlled to be substantially the same. Generally, the temperature of the gas passing through each of the respective plurality of lines 28 is equlibrated to be equal to that of the temperature of the block 42 as by passing the gas from each of the respective one of the plurality of lines 28 through a respective maze or contact path 44 and thence via a short conduit 46 to against the respective of the membranes 36.

As will be clear by reference to FIG. 1 each of the cavities 40 matingly holds a respective tube 32 therewithin. In contact with the block 42 and generally wrapped thereabout is a heater 48 for adjusting the temperature of the block and thereby the temperature of the tubes 32 and the solutions 12. Means are also provided for measuring the temperature of the block. In the embodiment illustrated these means comprise a thermocouple 50 or other temperature measuring device fitting within a well 52 in the block 42. A pair of electic leads 54 from the thermocouple 50 leads generally to a bridge circuit 56 which has a meter 58 on which temperature can be read out either directly or as an electrical quantity such as voltage or the like which can be easily converted into an equivalent temperature. A temperature adjusting knob 60 is provided for controlling the heater 48 so that the temperature of the block 42 and thus of each of the solutions 12 can be controlled to a desired value. An on-off switch 62 is also provided in line between the heater 48 and a wall plug 64 to assure that the machine can be easily and completely turned off when not in operation. It is clear that the simple bridge 56 along with the meter 58, temperature adjusting knob 60 and thermocouple 50 can be replaced with a feedback network whereby the temperature adjusting knob 60 can be set to any desired temperature and the heater 48 will then be controlled thereby in a feedback network to adjust the temperature of the block 42 until the temperature set on the meter 48 by the knob 60 is attained.

The structure of the block 42 is shown in considerably greater detail in FIGS. 3, 4 and 5. As previously mentioned, the block 42 is generally made of a heat conducting material such as copper or the like. The three cavities 40 are provided within the block 42 and generally extend to adjacent a bottom end 66 of the block 42. Each of the cavities 40 has a compressible member 68 which serves as compressible sealing means for sealing the respective cavity 40 to a respective exterior of the respective tube 24 and providing a compression force to hold the tube 24 within the cavity 40. Generally, the compressible sealing means will simply comprise a compressible O-ring or the like made of generally a plastic or preferably an elastomeric material such as, for example, Viton E60(a copolymer of hexafluoropropylene and vinylidenefluoride) or the like.

FIG. 4 most particularly illustrates a plurality of contact paths 44 which as previously mentioned serve to equilibrate the temperature of the gas flowing from the flow control means 16 and more particularly from the flow meters 22 to the respective of the sample tubes 32. In the embodiment illustrated in FIG. 4 there are three contact paths 44 provided. Gas from a respective one of the plurality of lines 28 enters a respective one of the contact paths 44 at an entrance 70 thereto, passes through the mazelike contact path 44 and then exits the contact path 44 at an exit 72 from whence it flows via a respective one of the conduits 46 to below a closed end 38 of the respective one of the tubes 24 and more particularly against a bottom side of one of the plurality of membranes 36. The compressible members 58, meanwhile, assures that the gas cannot escape around the respective one of the tubes 32 and up through the cavity 40 to the surrounding atmosphere. Thus, the only escape path for gas introduced via the conduit 46 is through the respective membrane 36. This aasures the build up of enough pressure below the respective one of the membranes 36 to assure gas flow will occur therethrough into the respective aqueous solution 12.

Turning now most particularly to the membranes 36 which comprise the preferred bubble delivering means of the invention it will be noted that each of these membranes comprise a porous member having a hydrophobic surface and that said porous member forms the bottom or closed end 38 of the respective one of the solution tubes 32. Each of the membranes 36 is impervious to flow of the aqueous solution therethrough when the solution tube 32 is filled with the aqueous solution 12 and is permeable to flow of the gas composition upwardly therethrough. Generally, each of the membranes 36 will have microscopic (capillary) paths therethrough and since the surface of the membranes 36 is hydrophobic the solution will not wet the microscopic capillary paths and thus will be held from flowing therethrough. On the other hand, gas will not be held up significantly by the microscopic or capillary paths and will simply pass upwardly therethrough against the head created by the respective of the solutions 12. Because of the relatively samll size of the capillaries leading through the membranes 36 the size of the bubbles introduced into the bottom of each of the solution tubes 32 will be extremely fine thus leading to very efficient surface to liquid contact as well as agitation whereby equilibrium will be extremely rapidly attained between the gas composition and the respective one of the solutions 12 through which it is being passed. More specifically, such equilibration has been found to take no more than about three or four minutes for a 10 cc. sample of aqueous solution 12. This is considerably less than the twenty to thirty minutes needed for equilibration of an aqueous solution using the fastest of the prior art apparatus for accomplishing this.

Referring now once again to FIG. 1 it will be apparent that each of the plurality of gas vessels 14 delivers the gas therefrom to a pressure regulator 74 before that gas is allowed to flow to a needle valve 18. Typically, the pressure within the gas vessel 14 might be several hundred psi while the pressure regulator 74 might provide for a pressure of no more than five psi. In this manner, the needle valves 18 are each operating with a constant upstream gas pressure head until the respective gas vessel 14 empties to below the pressure head to which the pressure regulator 74 is set. This assures that flow rates through the respective flow control means 16 are generally constant independent of the pressure within the respective bottles 14 so long as that pressure exceeds the setting of the pressure regulator 74.

Turning now most particularly to FIG. 6 it will be seen that the block 42 will generally be set within an insulating container 76 to assure proper and accurate temperature control.

FIGS. 7 and 8 illustrate a plate 78 which is made to abut the bottom 66 of the block 42 and to seal the three contact paths 44 each from the other. At a bottom side 80 of the plate 78 there are a plurality of nipples 82 to which the lines 28 are attachable. Also, the plate 78 has a hole 84 central therethrough which forms a continuation of the well 52.

Turning now to FIG. 9 there is illustrated an alternate embodiment of the invention wherein the block 42 has therein a single cavity 40 with a single aqueous solution 12 within a single solution tube 32. In this embodiment, the plate 78 which fits against the bottom 66 of the block 42 has a single nipple 82 extending therefrom which connects with a single line 28 from a single flow meter 22. The block 42 has a single maze or contact path 44 therewithin adjacent the bottom 66 thereof whereby the gas which flows through the line 28 is brought to the temperature of the block 42 before passing via a single conduit 46 to the bottom of the membrane 36 and then through the membrane and through the solution 12 therewithin. In a like manner to the embodiment shown in great detail in for example FIG. 6, a compressible member 68 is provided to form a gas tight fit between the solution tube 32 and the cavity 40. As will be noted, in the embodiment shown in FIG. 9 the thermocouple 50 enters the block 42 via a well 52 from a top 86 of the block 42 rather than from the bottom 66 thereof as in the embodiment illustrated most clearly in FIG. 6.

Turning now most particularly to FIGS. 10–13 there is illustrated therein a cell 30 in accordance with present invention which comprises the sample tube 32. It should generally be noted that the sample tube 32 is generally tapered from an upper end 88 thereof to a lower end 90 thereof so as to be generally frustoconical in shape whereby when it is placed in the respective one of the cavities 40 it can easily be inserted because of a relatively large fit at the top of a likewise tapered cavity 40. The tube 32 generally includes support means such as a support structure 92, in the embodiment illustrated a cross-shaped support structure 92 which is integrally and unitarily formed with the tube 32 interiorly of the tube 32 and abutting of the membrane 36 to prevent the membrane 36 from tearing. Generally the tube 32 will comprise a first polymeric material which is generally of a rigid nature. Any polymeric material may be used which will have the desired stiffness and be non-reactive to the aqueous solution contained therein and the gas bubbled through the respective one of the membranes 36. For example the tube 32 can be made of polyethylene, polypropylene, or any number of plastic materials having structural integrity (and referred to herein for convenience as rigid). Alternatively, the tube 32 can be made of any number of rigid (having structural integrity) elastomeric materials.

Generally, the membrane 36 will comprise a second polymeric material which may conceivably be chemically similar to or the same as the first polymeric material. The only requirement for the second polymeric material is that it be inert to the aqueous solution which would be held in contact therewith and to the gas which is to pass therethrough. Of course as previously mentioned the member 36 must provide a hydrophobic surface. Thus, the member 36 can be formed of a second polymeric material which is plastic in nature or elastomeric in nature so long as it has the necessary porosity to allow gas flow upwardly therethrough and the necessary hydrophobic character to prevent the aqueous solution 12 from flowing therethrough. For example, polyethylene, polypropylene and other polymeric membranes are particularly suitable as the membrane 36.

Turning now most particularly to FIG. 13 there is illustrated therein means for detachably attaching the membrane to the tube to form the lower closed end 38 of the tube 32. The particular detachable attaching means shown comprises a ring 94 which may itself be made of a rigid polymeric material or alternatively be made of metal and which fits matingly within a sleeve 96 which extends longitudinally from the closed end 38 of the tube 32 coaxially therewith. The ring 94 forms a mating fit within the sleeve 96 with the membrane 36 pressed therebetween. Generally, the tube 32 is made of a material that preferably is formable into said tube 32 by injection molding techniques so as to reduce the cost and time of production thereof.

In an apparatus 10 which includes a plurality of the tubes 32, the tubes 32 are preferably each coded as for example by making each of the tubes 32 a different color so that each of the tubes 32 when placed in a correspondingly coded one of the cavities 40 will receive a gas composition which originally came from a particularly known and coded one of the gas vessels 14. Thus for example one of the tubes 12 could conceivably be red in color and this tube 12 would then be aligned, for example, next to a red dot and would receive flow from a cylinder 14 which was coded to a red color. Alternatively to the use of color codes, one can of course use upraised bumps, markings, numerals or the like.

Turning now particularly to FIGS. 1, 2, 14 and 15 the structure of the gas vessels 14 and the interrelationship with the apparatus 10 as a whole will be explained in some detail. It is clear that each of the cylinders 14 is closed at a first end 98 thereof and has valve means such as a ball valve 100 adjacent a second end 102 thereof. The second end 102 of the cylinder 14 has extending longitudinally therefrom a threaded neck 104 of smaller diameter than the cylinder 14. The first end 98 of the cylinder 14 has extending longitudinally therefrom handle means, in the embodiment illustrated a handle 106, the handle 106 not extending radially significantly beyond the diameter of the cylinder 14. As will be most clear by reference to FIGS. 1 and 14 the handle 106 is preferably separately formed from the cylinder 14 and preferably includes fastening means 108 including a disc 110 extending to the diameter of the cylinder 14 and sleeve means such as a sleeve 112 which grippingly extends along an exterior surface 114 of the cylinder 14 a short distance in the direction of the second end 102 thereof. Thus, it is clear that the sleeve 112 fits tightly and grippingly about the exterior surface 114 of the cylinder 14 adjacent the first end 98 thereof. It is further clear that the handle 106 and the fastening means 108 which includes the disc 110 and the sleeve 112 generally comprises a unitary polymeric structure. It is preferred that the unitary polymeric structure comprise a rigid plastic or a rigid elastomer with the term rigid used again to connote structural integrity. As will be noted by reference to FIGS. 1 and 14 the handle 106 generally extends from the first end 98 of the cylinder 14 no more than at most one-third the length of the cylinder 14 and more generally no more than at most one-fifth the length thereof.

It should be noted that the ball valve 100 will generally be operated through the threaded neck 104 in a conventional manner.

Adverting again to FIGS. 1, 2, 14 and 15 it will be noted that a frame 116 of the apparatus 10 will generally include extending therefrom threaded fitting means such as the threaded female fittings 118 illustrated in FIG. 1. It is clear that the threaded fitting 118 is positioned to receive the threaded neck 104 of the cylinder 14 and the means that operate the ball valve 104 extend through the threaded neck 104 and into contact with the ball valve 100. As will further be noted most particularly be reference to FIGS. 1 and 14, there is formed within the frame 116 a cylindrical bore portion 120. In the case of apparatus which includes multiple cylinders 14 there will be a plurality of bores 120. An internal diameter of the cylindrical bore portion 120 is made substantially equal to and slightly greater than an external diameter of the cylinder 14. At the same time the threaded fitting 118 is positioned as by support means 122 and the pressure regulator 74 adjacent a first end 124 of the cylindrical bore portion 120 and generally along the axis of the cylindrical bore portion 120. In this manner, the cylinder 14 is insertable in the cylindrical bore portion 120 to align the threaded neck 104 with the threaded fitting 118 and the handle 106 is turnable to cause the threaded neck 104 to turn therewith and thread with the threaded fitting 118. As will further be noted by reference to FIGS. 1, 14 and 15 a second end 126 of the cylindrical bore portion 120 preferably includes an annulus 128 of a size and shape to accomodate the sleeve 112 of the fastening means 108. The handle 106 is generally restricted in size radially so as not to extend beyond the annulus 128. Thus it is clear that the bore 120 aligns the cylinder 14 for fast and proper threading between the neck 104 and the threaded fitting 118.

Each of the cylinders 14 along with the respective fastening means 108 and handle 106 forms a cylinder assembly 130. Each of the cylinder assemblies 130 in those apparatus 10 which include a plurality of cylinder assemblies 130 is generally coded to indicated into which respective one of said cylindrical bore portions 120 the particular cylinder assembly 130 is to be inserted. For example the respective handle 106, fastening means 108, and/or cylinder 14 can be color coded, can be numbered, or can otherwise be coded to correspond with coding which appears adjacent a respective one of the cylindrical bore portions 120.

Turning most particularly to FIGS. 1 and 14 it will be noted that a door 132 is generally provided as part of the frame 116, which door 132 is closable when the respective cylinder assemblies 130 are fully inserted within the respective of the cylindrical bore portions 120 and the respective of the threaded necks 104 are threaded within the respective of the threaded fittings 118. Thus, through use of the handle 106 attached to the back of the cylinder 14 one can make use of the alignment provided by the cylindrical bore portion 120 thus acquiring a blind or sightless fit of the neck 104 into threaded relationship with the threaded fitting 118 while at the same tiime allowing the door 132 to be closed fully thus providing no projecting parts from the frame 116 of the apparatus 10. This is clearly advantageous since the cylinders 114 are thus prevented from being damaged by their being completely enclosed within the respective of the cylindrical bore portions 120. In the absence of a handle such as 106 attached to the respective of the cylinders 14, the first end 98 of the respective cylinders 14 would potentially extend outwardly beyond the frame 116 thus exposing the cylinder 14 to possible damage and providing projecting parts on which an operator could be harmed.

While the invention has been described in connection with specific embodiments thereof, it will be understood that it is capable of further modification, and this application is intended to cover any variations, uses or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

That which is claimed is:

1. In an apparatus for equilibrating a hydrophilic liquid such as an aqueous solution with a gas composition which comprises a gas vessel having therewithin a gas of a selectable composition at a pressure above ambient atmospheric pressure, flow control means for receiving flow from said vessel and controlling a flow rate therefrom and conduit means leading from said flow control means to a solution cell having therewithin a hydrophilic liquid such as an aqueous solution, improved solution cell means providing extremely fast attainment of gas-solution equilibrium, comprising:

a removable tube of a polymeric material having an open end and a closed end, said closed end comprising a porous polymeric member having a hydrophobic surface, said member being impervious to flow of a hydrophilic liquid therethrough when said tube is filled therewith and positioned vertically with the closed end thereof downwardly and being permeable to pressurized flow of said gas composition upwardly therethrough.

2. Improved cell means as in claim 1, including means for removably securing said to said tube to form said closed end thereof.

3. Improved cell mans as in claim 1, wherein said tube comprises a first polymeric material.

4. Improved cell means as in claim 3, wherein said member comprises a second polymeric material.

5. Improved cell means as in claim 4, including support means abutting said member interiorly of said tube to prevent tearing of said member.

6. Improved cell means as in claim 5, wherein said member comprises a membrane.

7. Improved cell means as in claim 6, wherein said support means is unitarily formed as a part of said tube.

8. Improved cell means as in claim 7, wherein said removable securing means comprises a sleeve extending longitudinally from said closed end of said tube coaxially therewith and a ring fitting matingly within said sleeve with said membrane pressed between said sleeve and said ring.

9. Improved cell means as in claim 8, wherein said tube is frustoconically shaped and said closed end thereof has a smaller diameter than said open end thereof.

10. Improved cell means as in claim 1, including:
a second removable tube of a polymeric material having an open and a closed end, said closed end comprising a second porous polymeric member having a hydrophobic surface, said second member being impervious to flow of a second hydrohhilic liquid therethrough when said second tube is filled therewith and positioned vertically with the closed end thereof downwardly and being permeable to pressurized flow of a second composition from a second gas vessel upwardly therethrough.

11. Improved cell means as in claim 10, including means coding said first tube to receive said first gas composition from said first gas vessel and said second tube to receive said second gas composition from said second gas vessel.

12. Improved cell means as in claim 11, wherein said coding comprises providing a different color for each of said first and second tubes.

13. Improved cell means as in claim 1, including passage means communicating said conduit means with a bottom side of said member.

14. Improved cell means as in claim 13, including:
sealing means sealing said member in flow communication with said passage means.

15. Improved cell means as in claim 6, wherein said first polymeric material comprises a rigid plastic.

16. Improved cell means as in claim 15, wherein said rigid plastic is formable into said tube by injection molding techniques.

* * * * *